United States Patent
Yamaya et al.

(10) Patent No.: US 8,461,539 B2
(45) Date of Patent: Jun. 11, 2013

(54) COMBINED RADIATION THERAPY/PET APPARATUS

(75) Inventors: Taiga Yamaya, Chiba (JP); Hideo Murayama, Chiba (JP); Taku Inaniwa, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 178 days.

(21) Appl. No.: 12/996,471

(22) PCT Filed: Aug. 1, 2008

(86) PCT No.: PCT/JP2008/063862
§ 371 (c)(1),
(2), (4) Date: Dec. 6, 2010

(87) PCT Pub. No.: WO2010/013346
PCT Pub. Date: Feb. 4, 2010

(65) Prior Publication Data
US 2011/0092814 A1  Apr. 21, 2011

(51) Int. Cl.
*G01T 1/166*  (2006.01)
(52) U.S. Cl.
USPC .................. 250/363.05; 600/427; 250/363.02
(58) Field of Classification Search
USPC ....................................................... 600/427
See application file for complete search history.

(56) References Cited

U.S. PATENT DOCUMENTS 6,961,606 B2 * 11/2005 DeSilets et al. ............... 600/415
2003/0078488 A1 * 4/2003 DeSilets et al. ............... 600/407
2003/0153828 A1 * 8/2003 Kojima et al. ................ 600/425
2006/0293584 A1 * 12/2006 Kojima et al. ................ 600/407
2007/0153969 A1 * 7/2007 Maschke .......................... 378/4

FOREIGN PATENT DOCUMENTS

| JP | U-2-48888 | 4/1990 |
| JP | A-4-268484 | 9/1992 |
| JP | A-9-211130 | 8/1997 |
| JP | A-2001-141827 | 5/2001 |
| JP | A-2001-346773 | 12/2001 |
| JP | A-2004-166975 | 6/2004 |
| JP | A-2005-52308 | 3/2005 |
| JP | A-2006-513410 | 4/2006 |
| JP | A-2007-3264 | 1/2007 |

(Continued)

OTHER PUBLICATIONS

Enghardt, W. et al., "Charged Hadron Tumour Therapy Monitoring By Means of PET," *Nuclear Instruments and Methods in Physics Research*, Section A, 2004, pp. 284-288, vol. 525.

Janek, S. et al., "Development of Dose Delivery Verification by PET Imaging of Photonuclear Reactions Following High Energy Photon Therapy," *Physics in Medicine and Biology*, 2006, pp. 5769-5783, vol. 51.

(Continued)

*Primary Examiner* — Unsu Jung
*Assistant Examiner* — Saurel J Selkin
(74) *Attorney, Agent, or Firm* — Oliff & Berridge, PLC

(57) ABSTRACT

A combined radiation therapy/PET apparatus includes: an open PET device having multi-ring detector rings that are opposed to each other in the direction of the body axis so as to leave a gap therebetween; and a radiation therapy apparatus for performing radiation therapy through the gap. When imaging the condition of an affected area and a treatment beam for monitoring in radiation therapy of irradiating the affected area with X-rays, gamma rays, or particle beams, the apparatus covers a region of interest in the irradiation field of the radiation therapy with the field-of-view of the open PET device, thereby making possible the positioning of the irradiation field and treatment monitoring using PET images.

7 Claims, 17 Drawing Sheets

FOREIGN PATENT DOCUMENTS

| JP | A-2007-111535 | 5/2007 |
| JP | A-2008-134205 | 6/2008 |
| JP | A-2008-173297 | 7/2008 |

OTHER PUBLICATIONS

Crespo, P. et al., "On the Detector Arrangement for In-Beam PET for Hadron Therapy Monitoring," *Physics in Medicine and Biology*, 2006, pp. 2143-2163, vol. 51.

Yamaya, T. et al., "A Proposal of An Open PET Geometry," *Physics in Medicine and Biology*, 2008, pp. 757-773, vol. 53.

International Search Report issued in International Application No. PCT/JP2008/063862 on Oct. 7, 2008 (with translation).

Yamaguchi et al. "Development of Molecular Imaging Device for Patient Setup: Preliminary Simulation of Open-PET" Hokkaido University Graduate School of Medicine. vol. 28 Supplement No. 2 Apr. 2008. (with partial translation).

* cited by examiner

SD: Single event data
LD: List mode data
HD: Histogram data
ID: Image data

COMBINED RADIATION THERAPY/PET APPARATUS

TECHNICAL FIELD

The present invention relates to a combined radiation therapy/PET apparatus which can image the condition of an affected area and a treatment beam for monitoring in radiation therapy of irradiating the affected area with X-rays, gamma rays, or particle beams.

BACKGROUND ART

Positron emission tomography (PET) is attracting attention as an effective test method for earlier diagnosis of cancer, cerebrovascular disease, dementia, etc. In PET, a compound labeled with a trace amount of positron emitting nuclides is administered and annihilation radiation emitted from inside the body is detected to create an image of biological functions such as sugar metabolism and check for a disease and its extent. PET devices for practicing PET have been put into actual use.

The principle of PET will be described below. Positron emitted from a positron emitting nuclide by positron decay is annihilated with ambient electron to produce a pair of 511-keV annihilation radiations, which are measured by a pair of radiation detectors based on the principle of coincidence counting. The position of the nuclide can thus be located on a single line (coincidence line) that connects the pair of detectors. An axis from the patient's head to feet will be defined as a body axis. The distribution of nuclides on a plane that perpendicularly crosses the body axis is determined by two-dimensional image reconstruction from data on coincidence lines on the plane, measured in various directions.

Early PET devices therefore have had a single-ring detector in which detectors are closely arranged in a ring shape on a plane to be the field-of-view so as to surround the field-of-view. With the advent of a multi-ring detector which includes a lot of single-ring detectors closely arranged in the direction of the body axis, the two-dimensional field-of-view has subsequently been extended to three dimensions. Since 1990's, 3D mode PET devices have been actively developed which perform coincidence measurement even between different detector rings with a significant improvement in sensitivity.

For cancer detected by the PET diagnosis or the like, treatments have a critical role. Approaches other than surgical operations and medication include radiation therapy of irradiating the affected area with radiations such as X-rays and gamma rays. In particular, particle radiotherapy of irradiating only a cancerous area with a heavy particle beam or proton beam is attracting much attention as a method both with an excellent treatment effect and a sharply concentrated irradiation characteristic with respect to the affected area. For irradiation, the direction and dose of the beam are precisely controlled according to a treatment plan which is thoroughly calculated based on X-ray CT images or the like obtained separately.

The patient positioning accuracy is the key to administer treatment in precise accordance with the treatment plan. The irradiation field is often positioned based on an X-ray image. In general, X-ray images fail to provide a sufficient contrast between tumor and normal tissue, and it is difficult to identify a tumor itself for positioning. In addition to such misalignment of the irradiation field at the time of patient setup, other problems have been pointed out such as a change in the tumor size from the time of creation of the treatment plan, and respiratory and other movements of the tumor position. Under the present circumstances, it is difficult to accurately identify whether irradiation is performed according to the treatment plan. Even if the actual irradiation field deviates from the treatment plan, it is not easy to detect.

To solve the foregoing problems, attention is being given to methods of imaging the irradiation field in real time using the PET techniques. In one study, fludeoxyglucose (FDG) or other PET medicine for use in cancer diagnosis is administered before treatment. Using a PET device installed in combination with the treatment device, imaging is performed to directly observe the tumor position while positioning the irradiation field. In another method, no PET medicine is administered. Instead, annihilation radiations occurring from a projectile fragmentation reaction, target fragmentation reaction, and/or photonuclear reaction in particle beam irradiation or X-ray irradiation are rendered into an image by using the principle of PET. Therapy monitoring is possible since the position of occurrence of the annihilation radiations has a strong correlation with the dose distribution of the irradiation beam (W. Enghardt et al., "Charged hadron tumour therapy monitoring by means of PET," Nucl. Instrum. Methods A 525, pp. 284-288, 2004. S. Janek et al., "Development of dose delivery verification by PET imaging of photonuclear reactions following high energy photon therapy," Phys. Med. Biol., vol. 51 (2006) pp. 5769-5783).

If a new PET medicine that allows an immediate evaluation of the activity of tumor cells and normal cells is put to actual use in the future, it will be possible to not only image the tumor position and the dose distribution but also monitor the effect of treatment on tumor cells and the impact on ambient normal cells in real time for more appropriate irradiation control.

In an ordinary PET device, detectors are arranged in a ring-like configuration. To install the detectors in combination with a treatment device, they need to be arranged so as not to block the treatment beam. Studies have so far been made on an opposed gamma camera type PET device in which two flat PET detectors are installed across the bed of the treatment device. Such a PET device has had an essential problem that the detector gap causes a lack of information necessary for image reconstruction, resulting in nonuniform resolution and lower device sensitivity (P. Crespo et al., "On the detector arrangement for in-beam PET for hadron therapy monitoring," Phys. Med. Biol., vol. 51 (2006) pp. 2143-2163, and Satoshi Yamaguchi et al, "Development of molecular imaging device for patient setup—A basic simulation on Open-PET device—," Japanese Journal of Medical Physics, Vol. 28, Sup. 2 (2008) pp. 256-257).

To improve the sensitivity of a PET device, as illustrated in FIG. 1(a), the detectors need to be closely arranged in a tunnel-like configuration to form a multi-ring detector 10 with an increased solid angle. The long tunnel-shaped patient port, however, increases psychological stress on the patient 6 under examination as well as obstructs the patient's treatment. In view of this, as illustrated in FIG. 1(b), the applicant has proposed an open PET device in which a plurality of multi-ring detectors (also referred to as detector rings) 11 and 12 split in the direction of the body axis of the patient 6 are arranged apart from each other to provide a physically opened area of field-of-view (also referred to as an open field-of-view). As shown in FIG. 2, images in the open area are reconstructed from the coincidence lines between the remaining multi-ring detectors 11 and 12. In the diagram, 8 represents a bed.

As shown in FIGS. 1(b) and 2, the open PET device is designed to have two split detectors of identical width (Taiga Yamaya, Taku Inaniwa, Shinichi Minohara, Eiji Yoshida, Naoko Inadama, Fumihiko Nishikido, Kengo Shibuya, Chih Fung Lam and Hideo Murayama, "A proposal of an open PET geometry," Phy. Med. Biol., 53, pp. 757-773, 2008). The open PET device is suitable for monitoring in radiation therapy since the beam irradiation can be performed without interfering with the detectors.

As shown in FIG. 3, the field-of-view is 2W+G in the direction of the body axis, where W is the dimension (also referred to as width) of the detector rings 11 and 12 in the direction of the body axis, and G is the dimension (also referred to as gap) of the intervening open area in the direction of the body axis. As shown in FIG. 3(c), if the open area gap G exceeds W, the imaging area becomes discontinuous in the direction of the body axis. The upper limit of the open area gap G to obtain a field-of-view continuous in the direction of the body axis is thus W as shown in FIG. 3(b). The sensitivity concentrates at the center of the open area and drops significantly in the periphery of the open area. To suppress the extreme sensitivity drops at both ends of the open area, G needs to be set smaller than W as shown in FIG. 3(a). This, however, narrows the open area gap and the field-of-view in the direction of the body axis (see the foregoing document).

Since the open PET device previously proposed by the applicant has had the problem that the sensitivity concentrates at the center of the open area and drops significantly in the periphery of the open area, it has been needed to increase W relative to G in order to suppress the local sensitivity drops. Since the open area gap is limited by W, it has been needed to increase W itself in order to increase the open area gap further. However, there has been the problem that the increased number of detectors to constitute each multi-ring detector makes the device higher in price, larger in size, and more complicated in configuration.

In particular, when the open PET device is used to perform monitoring in particle radiotherapy, the beam irradiation may cause a performance drop or a failure of the detectors in cases such as when the detector circuit itself is affected. During the beam irradiation, the detectors therefore need to be separated from the irradiation field by several tens of centimeters. In order to expand the open area gap G, as mentioned previously, the dimension W of the detectors in the direction of the body axis need to be increased. Such an increase undesirably results in higher price, larger size, and further complication of the device. The detectors may alternatively be moved to near the irradiation field for PET measurement after the end of the irradiation. This, however, has the problem that the patient's binding time increases as much as the moving time. In addition, nuclides produced by the beam irradiation have an extremely short half-life of about several tens of seconds to 20 minutes, and the nuclides can even move within the living body due to the blood flow and other factors. It is therefore desirable to start PET measurement immediately after the irradiation.

DISCLOSURE OF THE INVENTION

The present invention has been achieved in view of the foregoing conventional problems. It is thus an object of the present invention to create an image of an affected area and a treatment beam for monitoring in radiation therapy of irradiating the affected area with X-rays, gamma rays, or particle beams.

(1) On the Relationship Between the Open Field-of-View and the Irradiation Field FIG. 4 shows an open PET device which includes a first detector ring 11 and a second detector ring 12. The first detector ring 11 has a ring diameter of D1 and a sensitivity area width of W1 in the direction of the body axis. The second detector ring 12 has a ring diameter of D2 and a sensitivity area width of W2 in the direction of the body axis. The gap between the detector rings is G. FIG. 4 shows a case where there are dead regions due to too large G. As discussed in the document (Taiga Yamaya, Taku Inaniwa, Shinichi Minohara, Eiji Yoshida, Naoko Inadama, Fumihiko Nishikido, Kengo Shibuya, Chih Fung Lam and Hideo Murayama, "A proposal of an open PET geometry," Phy. Med. Biol., 53, pp. 757-773, 2008), the dead regions occurring in the field-of-view produce an artifact around the dead regions in the image.

If the nuclide distribution, i.e., the irradiation field falls within the field-of-view of cylindrical shape (referred to as an open field-of-view) having a diameter of DO and a length of WO, it is possible to image the irradiation field without being affected by dead regions irrespective of the value of G. DO and WO are calculated by the following equations:

$$WO=(D1 \times W2+D2 \times W1)/(D1+D2) \tag{1}$$

$$DO=D1 \times D2 \times WO/(D1 \times H2+D2 \times H1) \tag{2}$$

$$H1=D1 \times (G+W2)/(D1+D2) \tag{3}$$

$$H2=D2 \times (G+W1)/(D1+D2) \tag{4}$$

If the first detector ring 11 and the second detector ring 12 have the same size, i.e., D1=D2 and W1=W2, the open field-of-view has a diameter and length of:

$$WO=W1, \text{ and}$$

$$DO=W1 \times D1/(G+W1).$$

(2) On the Increase of W1 and W2

In order to expand the open field-of-view, it is needed to increase W1 and W2 themselves which are the fields of view of the first and second detector rings in the direction of the body axis. W1 and W2 can be increased with no increase in the actual number of detectors by dividing the detector rings into smaller units of detector rings and arranging the units apart in the direction of the body axis.

As shown in step 1 of FIG. 5, an element detector ring 11 that is composed of detection elements or detection element blocks having a width of W will be referred to as a unit [0]. The entire configuration of D units [0] arranged at intervals of αW will be referred to as a first level unit [1]. The unit [1] has a width of W[1]=(D+(D−1)α)W.

Next, as shown in step 2 of FIG. 5, the entire configuration of D units [1] arranged at intervals of αW[1] will be referred to as a second level unit [2]. The unit [2] has a width of W[2]=(D+(D−1)α)²W.

The foregoing step is repeated a total of N times to obtain the Nth level unit [N] as shown in step N of FIG. 5. That is, the field-of-view in the direction of the body axis, (D+(D−1)α)$^N$W, can be covered by element detector rings as much as a width of D$^N$W.

Here, the scaling factor of the view expansion will be defined as {(D+(D−1)α)/D}$^N$. For example, given D=2 and α=0.5, the scaling factor is approximately 3 times for N=5, approximately 9 times for N=10, and approximately 87 times for N=20.

α a is a parameter for adjusting the balance between the effect of expanding the field-of-view in the direction of the body axis and the effect of reducing non-uniformity in sensitivity. α may be changed unit by unit or step by step within the range of 0<α≦1. Smaller α suppresses local sensitivity drops, but reduces the effect of expanding the field-of-view in the direction of the body axis. α fixed at the maximum value of 1, on the other hand, maximizes the field-of-view in the direction of the body axis, but with a higher emphasis on local sensitivity drops.

The foregoing description has dealt with the case where the width W of the element detector ring, the number D of units arranged in a step, and α are constant in value. However, W need not be uniform, nor need be α or D fixed in each step.

A technical idea apparently similar to the present invention has been proposed in which detectors are sparsely arranged with gaps so that coincidence lines are sampled at a reduced density for higher uniformity and an expanded area of the field-of-view (See Japanese Patent Application Laid-Open No. Hei 9-211130 and Japanese Patent Application Laid-Open No. 2001-141827). In particular, Japanese Patent Application Laid-Open No. Hei 9-211130 clearly states that detectors having a light receiving surface of W in width are arranged in one direction so as to satisfy W≦L≦2W and L'=2L, where L is the distance between the center of the light receiving surface of a detector at an end and that of the adjoining detector, and L' is the distance between the centers of the light receiving surfaces of arbitrary adjoining detectors except those at the ends. L' has a maximum value of 4W, which means that the distance between the ends of the light receiving surfaces of the adjoining detectors is 3W.

Such a technical idea, however, is conceived for a positron imaging device of planar imaging, and does not include any mention to a PET device which is a tomographic device of fundamentally different imaging principle. If detectors are sparsely arranged on the rings according to the technical idea, the image quality will inevitably drop due to a lack of coincidence lines necessary for image reconstruction. Alternatively, if detectors are closely arranged on the rings but the individual single-ring detectors are sparsely arranged with the application of the technical idea only to the direction of the body axis, such a PET device will not be much beneficial since the scaling factor of the field-of-view in the direction of the body axis is limited to approximately twice at most.

The present invention has been achieved in view of the foregoing findings, and provides a combined radiation therapy/PET apparatus which includes: an open PET device having multi-ring detector rings that are opposed to each other in a direction of a body axis so as to leave a gap greater than a width of each detector ring therebetween; and a radiation therapy device that irradiates an affected area with a radiation beam through the gap for radiation therapy, a region of interest lying in an irradiation field of the radiation therapy being covered by a field-of-view of the open PET device so as to allow positioning of the irradiation field, beam monitoring, and treatment monitoring using a PET image.

Here, the entire irradiation field may be covered by the field-of-view of the PET device.

In the detector rings, a predetermined number of element detector units each including a predetermined number of detection element rings may be arranged with a gap therebetween so that the gap is smaller than or equal to an average width of two element detector units that form the gap.

In the detector rings, a predetermined number of element detector units each including a predetermined number of detection element rings may be arranged with a gap therebetween. A first ring set in which the gap is smaller than or equal to an average width of two element detector units that form the gap and a second ring set that includes a predetermined number of element detector units may be arranged to leave a gap of or less than an average of the widths of the first ring set and the second ring set.

A gap of the open PET device in the direction of the body axis may be variable.

In the open PET device, if a first detector ring and a second detector ring divided by a gap that includes the irradiation field have the same size with a diameter of D1=D2 and a length of W1=W2 and are arranged with a gap of G therebetween, an open field-of-view may have a diameter and length of:

$$WO = W1, \text{ and}$$

$$DO = W1 \times D1/(G+W1).$$

In the open PET device, when the first detector ring and the second detector ring form a gap that includes the irradiation field, coincidence measurement may be performed only between the first detector ring and the second detector ring, not within the first detector ring or within the second detector ring.

In respiratory-gated irradiation of performing irradiation with the radiation beam in synchronization with a respiratory phase, measurement may be performed in time with intervals between beam irradiations.

The configuration of the detector rings may be changed from one detector ring to another.

BEST MODE FOR CARRYING OUT THE INVENTION

Hereinafter, embodiments of the present invention will be described in detail with reference to the drawings.

Figure 1:
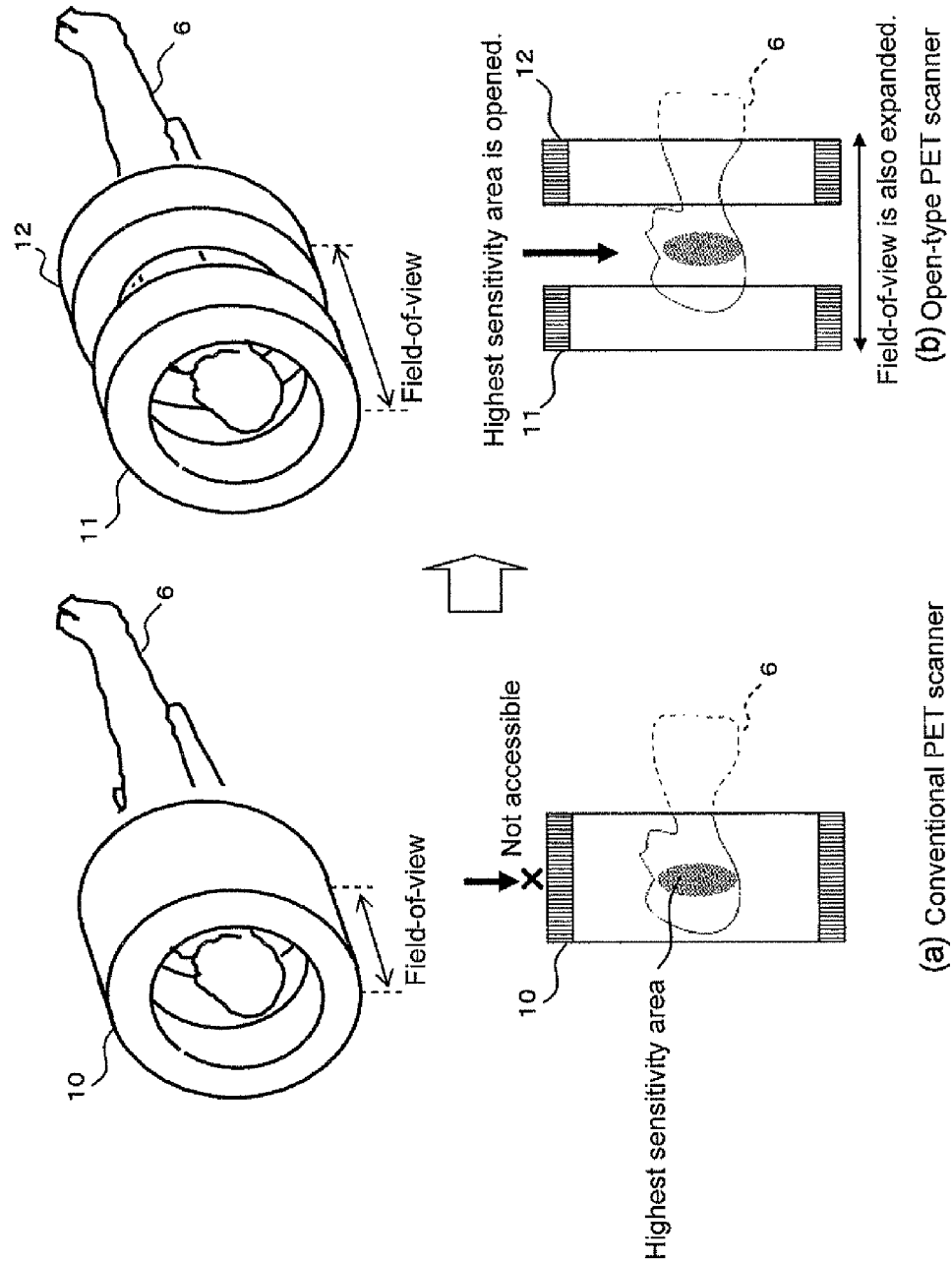
FIG. 1(a) includes a perspective view and a cross-sectional view showing the configuration of a conventional typical PET device, and FIG. 1(b) includes a perspective view and a cross-sectional view showing the configuration of an open PET device that has previously been proposed by the applicant.
Figure 2:
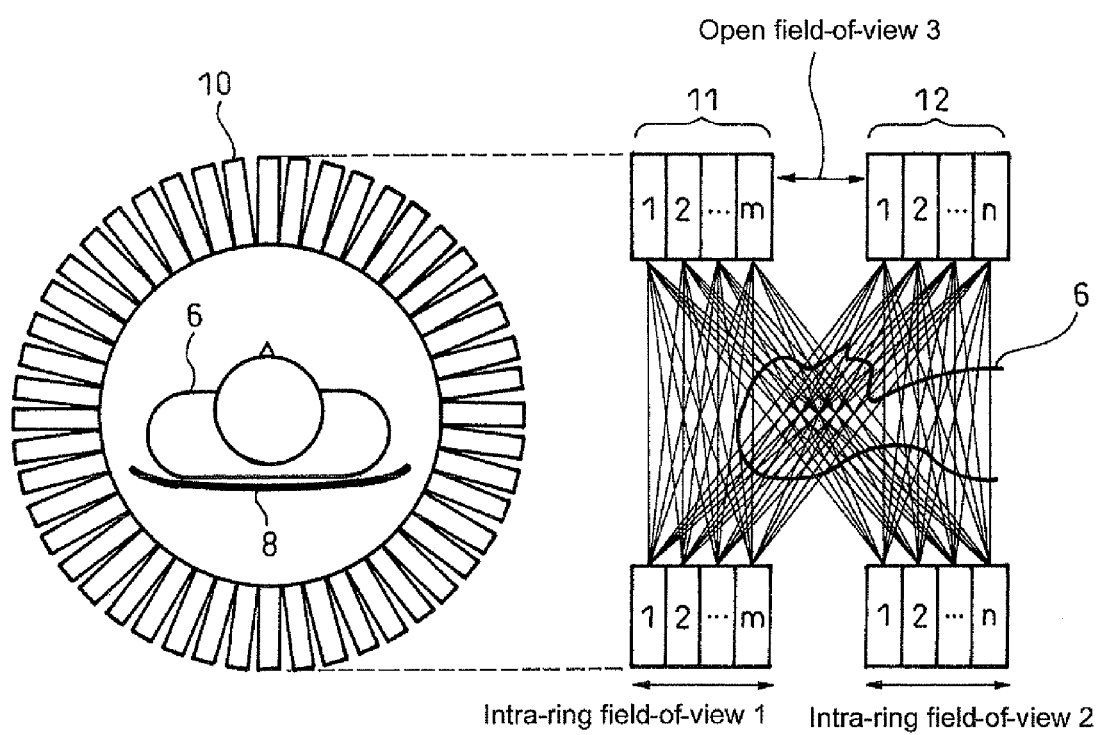
FIG. 2 is a cross-sectional view showing the principle of image reconstruction in an open PET device.
Figure 3:
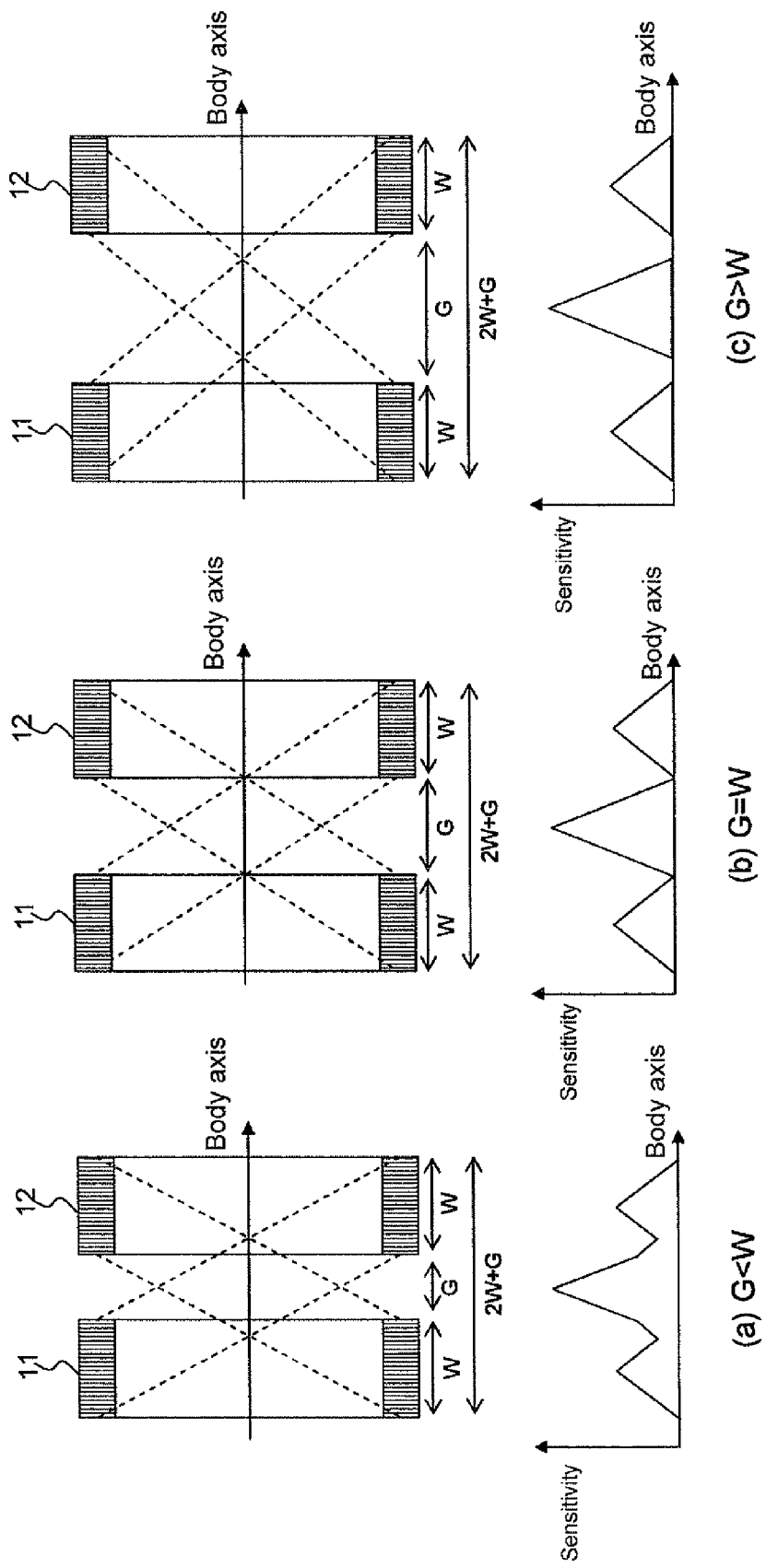
FIG. 3 includes cross-sectional views and graphs showing the relationship between the open area gap and sensitivity of an open PET device.
Figure 4:
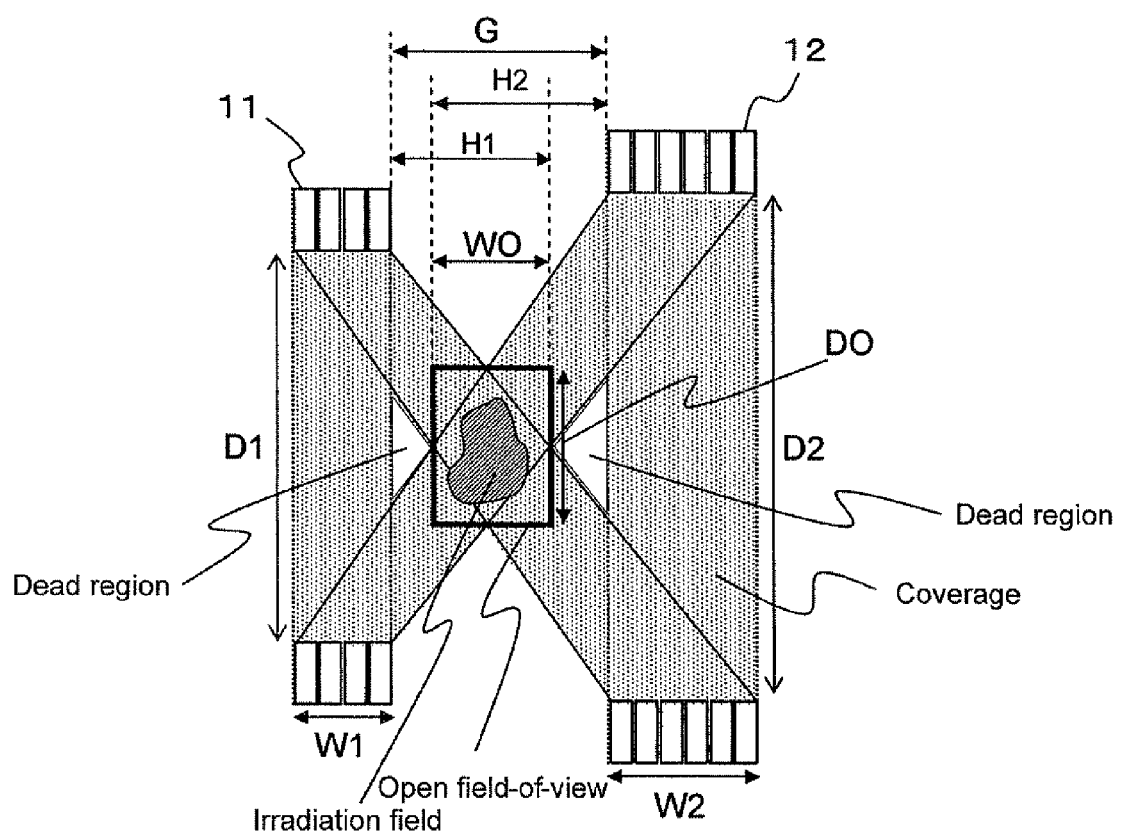
FIG. 4 is a diagram showing the relationship between an open field-of-view and an irradiation field.
Figure 5:
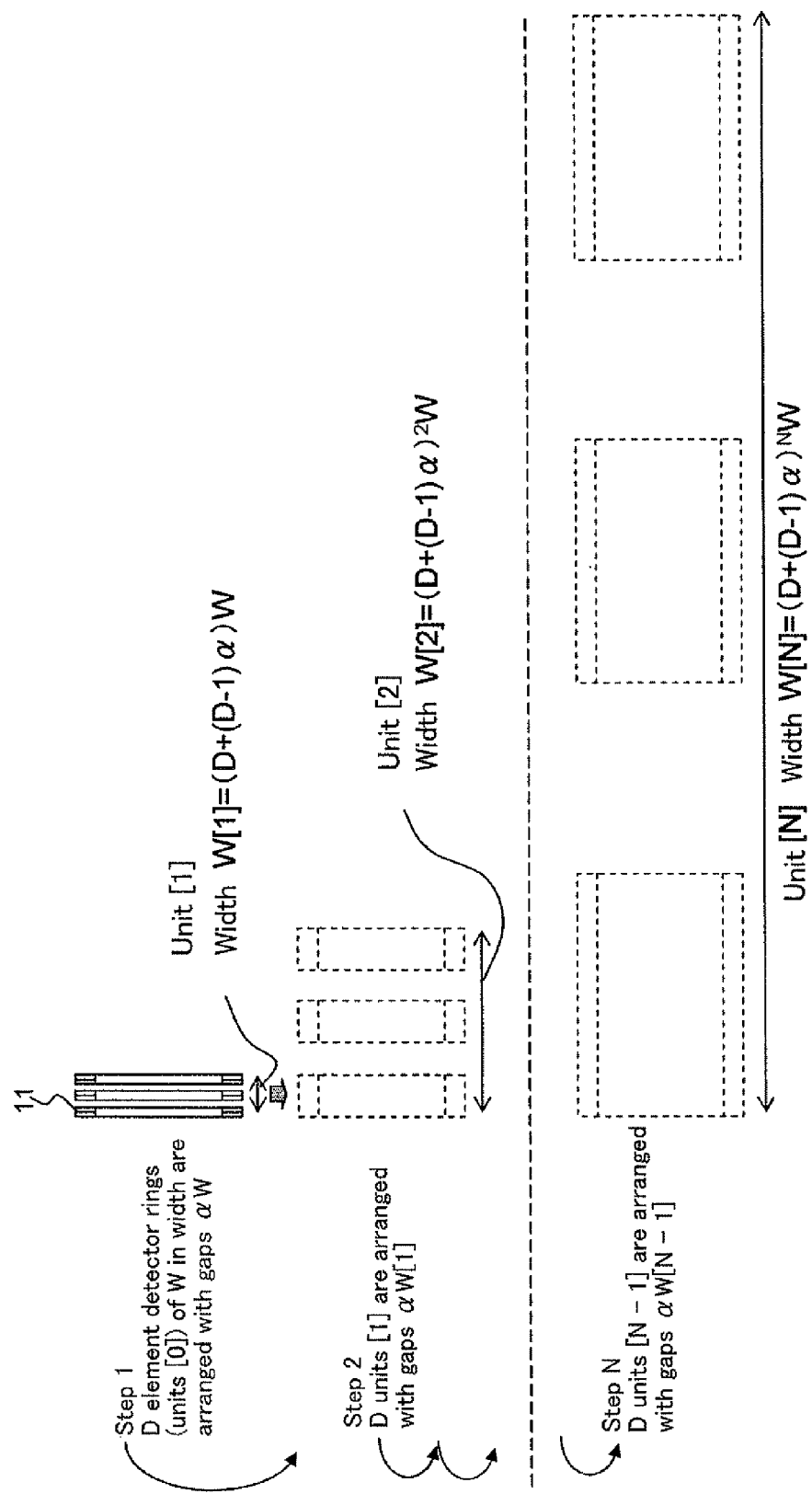
FIG. 5 is a diagram showing a method of expanding the open field-of-view.
Figure 6:
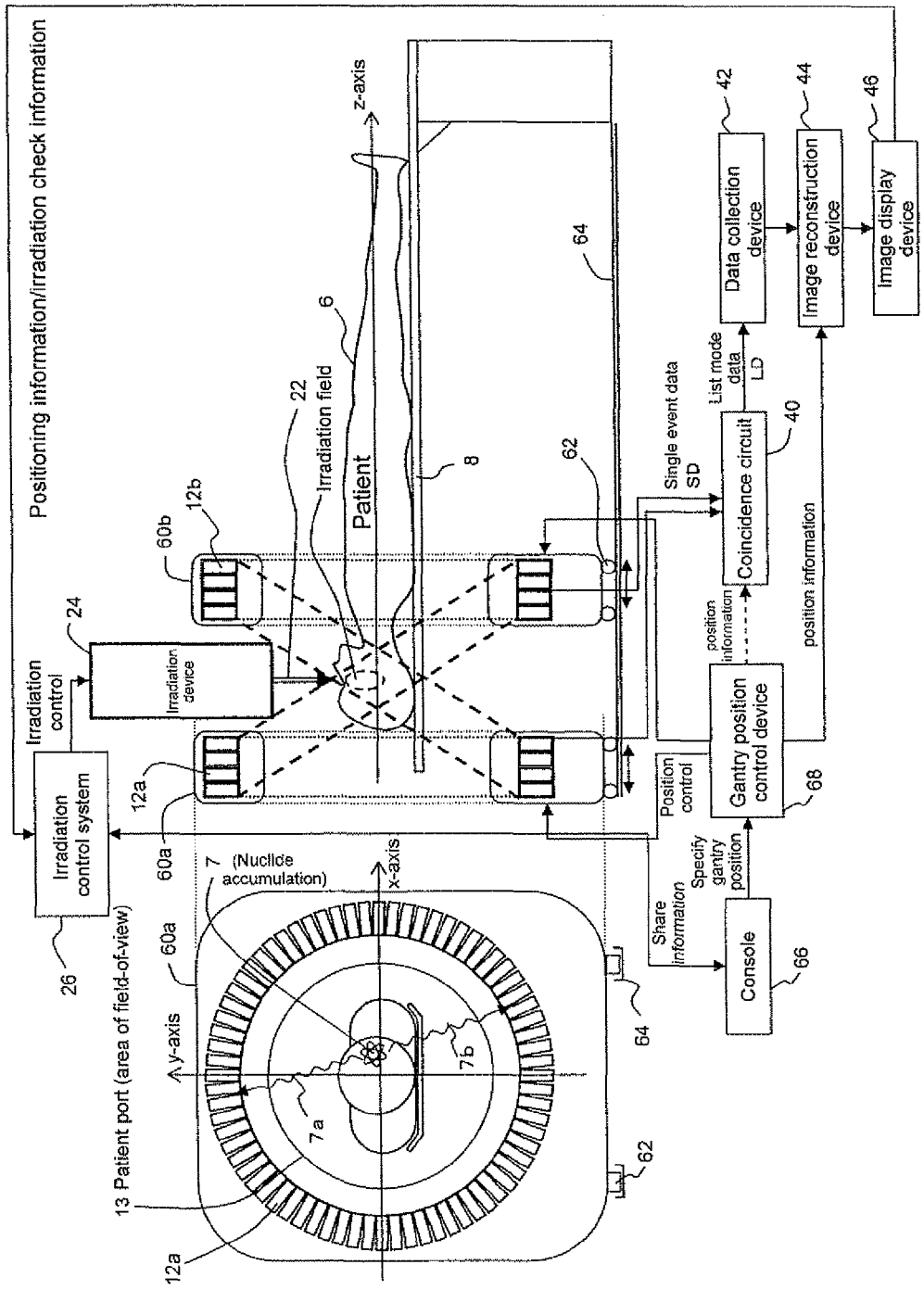
FIG. 6 is a diagram showing the configuration of a first embodiment of the present invention.

FIG. 6 shows the configuration of a first embodiment. Two identical ring-shaped detector rings 12a and 12b are arranged in parallel as independent gantries (60a, 60b), and a radiation irradiation device 24 is interposed between the detector rings 12a and 12b. This implements the treatment monitoring of observing the same area at the same time as treatment by PET. While the positions of the detector rings 12a and 12b may be fixed with respect to a bed 8 and the irradiation device 24, the detector rings here are configured to form a variable gap therebetween.

Specifically, the embodiment includes the detector rings 12a and 12b, gantry covers 60a and 60b which cover the respective detector rings, and the bed 8 on which a patient 6 lies. The gantries are each equipped with wheels 62, and have the function of moving back and forth on common or different rails 64.

To shift the open field-of-view in the direction of the body axis, the detector rings 12a and 12b are moved with respect to the fixed bed 8, or the bed 8 is moved with the detector rings 12a and 12b fixed.

A treatment beam 22 produced from the radiation irradiation device 24 passes through the gap area between the detector rings 12a and 12b, and is projected toward the irradiation field of the patient 6 without interfering with the PET gantries (60a, 60b). The radiation irradiation device 24 is controlled by an irradiation device control system 26. The gap between the detector rings 12a and 12b is determined with a margin so that the treatment beam 22 will not interfere with the PET gantries (60a, 60b) nor will fragments produced by the beam affect the detectors. PET images obtained are fed back to the irradiation device control system 26 and used for positioning the irradiation field, checking the effect of the treatment, and modifying the treatment plan.

Next, the method of processing the measured data will be described. Nuclides 7 in the body of the patient 6 emit pairs of annihilation radiations 7a and 7b which travel at angles of approximately 180° from each other in all directions. Single event data SD, which is the measured data on either one of a pair of annihilation radiations 7a and 7b, is transmitted from the detector rings 12a and 12b to a common coincidence circuit 40. The single event data SD is converted into list mode data LD which is the information on the coincidence pair between the detector rings 12a and 12b.

The list mode data LD is stored into a recording medium by a data collection device 42 before transmitted to an image reconstruction device 44 for image reconstruction operation. The reconstructed image is then displayed by an image display device 46.

The movement of the detector rings 12a and 12b is controlled by the gantry position control device 68 based on gantry position information which is specified from a console device 66. The gantry position information is either included into the list mode data LD through the coincidence circuit 40 or directly transmitted to the image reconstruction device 44 so that the calculation for image reconstruction operation can be performed based on the actual position information on the detectors.

It is known that the beam irradiation can produce a large amount of prompt gamma rays which serve as noise components to the PET measurement. The PET measurement data under the beam irradiation is not suitable for imaging. To prevent load on the data collection system, it is therefore desirable to collect data after the selection of only data for image reconstruction use. If the data collection system has sufficient capacity, the data collection may be performed all the time with the data selection processing at the stage prior to the image reconstruction.

Figure 7:
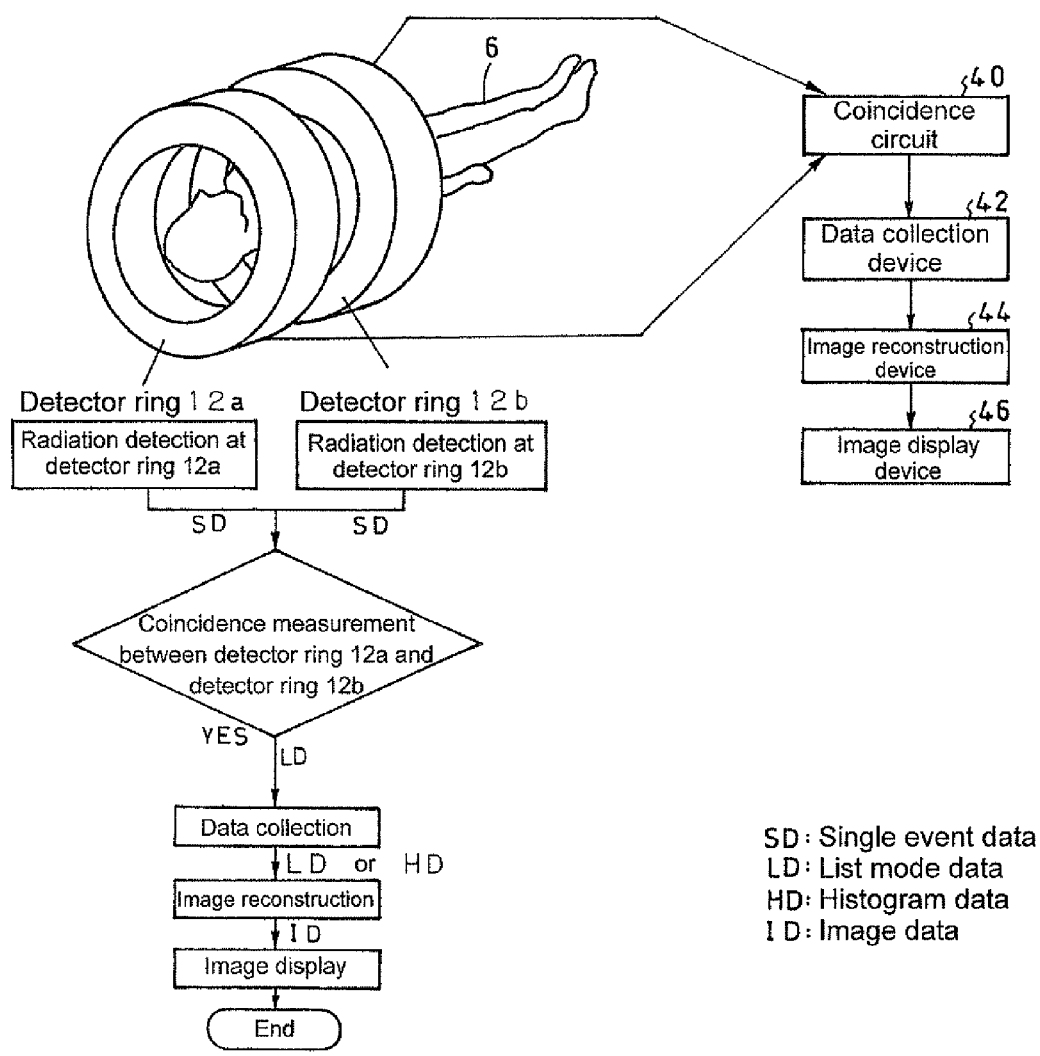
FIG. 7 is a diagram showing the operation of the first embodiment.

Next, the operation of the first embodiment will be described with reference to FIG. 7.

The present embodiment not only performs coincidence measurement between part or all of the detector pairs that connect the first detector ring 12a and the second detector ring 12b, but also can perform coincidence measurement between part or all of the detector pairs within the first detector ring 12a and between part or all of the detector pairs within the second detector ring 12b. To image the open field-of-view alone, however, coincidence measurement only between the first detector ring 12a and the second detector ring 12b is sufficient. Since unnecessary single event data SD can be excluded from the data stream, it is possible to improve the throughput and increase the dynamic range. The resulting list mode data LD is imaged through the data collection device 42 and the image reconstruction device 44.

Next, based on a commercially available PET device, a computer simulation was performed with detector rings arranged on the right and left. The detector rings (sensitivity area width W=153.6 mm in the direction of the body axis) were composed of 32 detection element rings (4.8 mm in width) each including 576 detection elements (scintillators) arranged on a circumference with a diameter of 827 mm. The simulation was performed for a case where the gap G between the right and left detector rings was at the upper limit with no dead region, or G=W, and for a case where the gap G exceeds the upper limit, or G=2W. The numerical phantoms used in the simulation were a cylindrical phantom greater than the open field-of-view and a spherical phantom lying within the open field-of-view. The cylindrical phantom was a uniform cylindrical source (230 mm in diameter, 614.4 mm in length) including 63 spots of 4.0 mm in diameter. The cylinder-to-spot contrast ratio was 1:5. The spherical phantom was a spherical source of 120 mm in diameter, including nine spots of 10 mm in diameter and two spots of 30 mm in diameter. The sphere-to-spot contrast ratio was 1:3.

Figure 8:
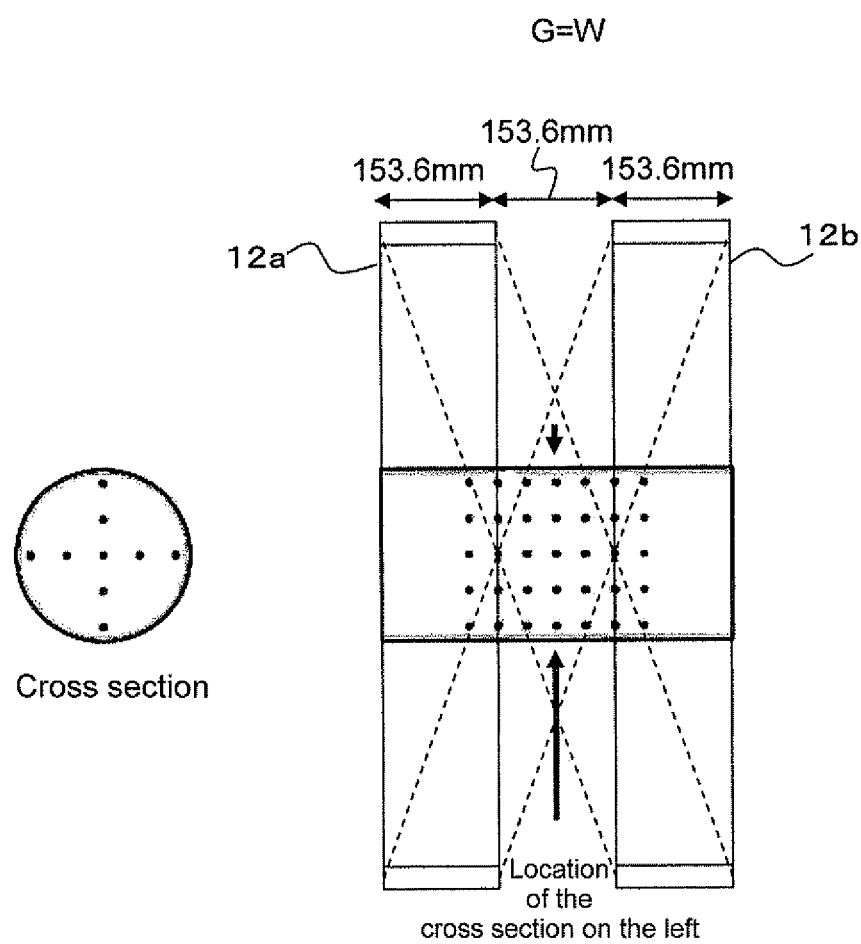
FIG. 8 is a diagram showing the arrangement of detectors and a cross section of the reconstructed image when measuring a cylindrical phantom with G=W.
Figure 9:
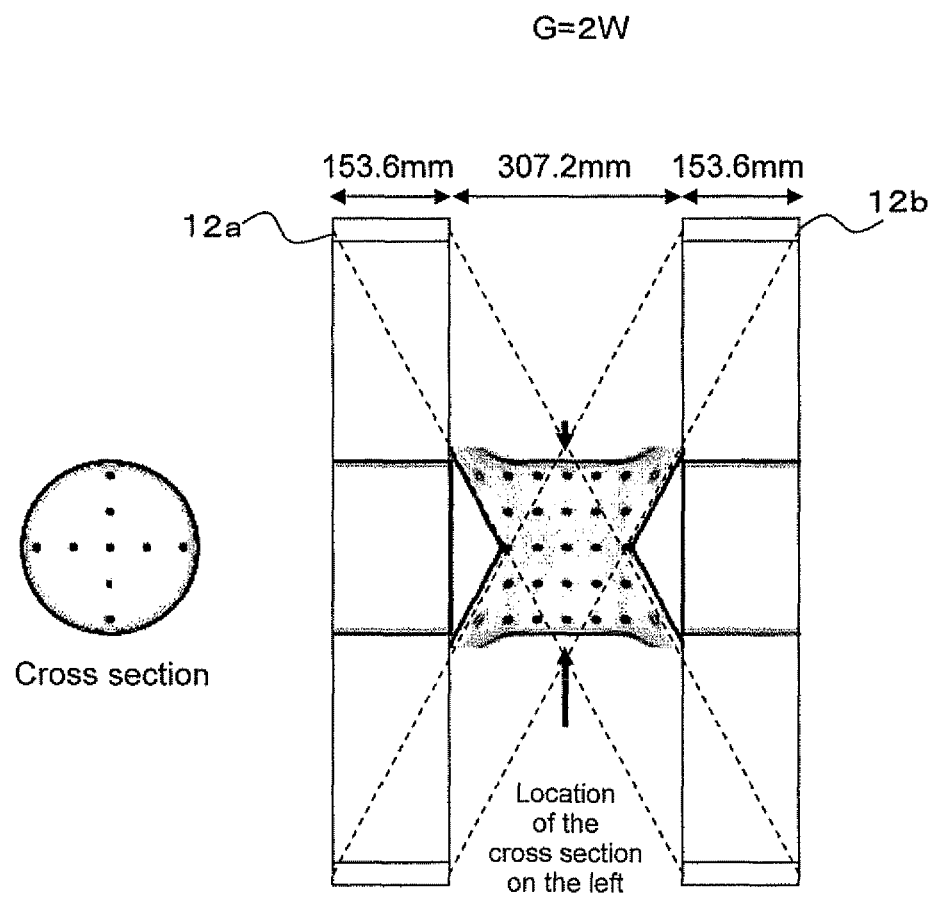
FIG. 9 is a diagram showing the arrangement of the detectors and a cross section of the reconstructed image when measuring the cylindrical phantom with G=2W.

FIGS. 8 to 11 show the arrangement of the detectors and a cross section of the reconstructed image. For improved visibility, the cross-sectional images displayed are given contour enhancement processing. FIG. 8 shows the result of measurement of the cylindrical phantom under the condition of G=W. FIG. 9 shows the result of measurement of the cylindrical phantom under the condition of G=2W. It can be seen that the object, i.e., the irradiation field greater than the open field-of-view cannot be properly imaged due to the dead regions occurring if G exceeds W.

Figure 10:
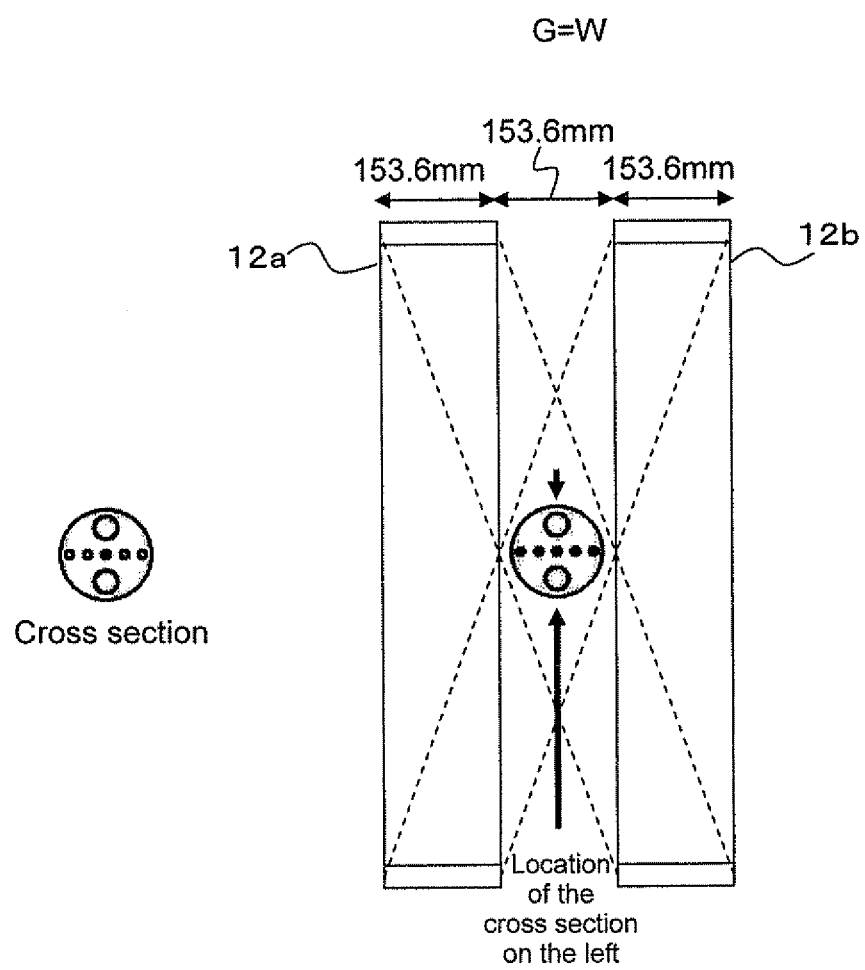
FIG. 10 is a diagram showing the arrangement of the detectors and a cross section of the reconstructed image when measuring a spherical phantom with G=W.
Figure 11:
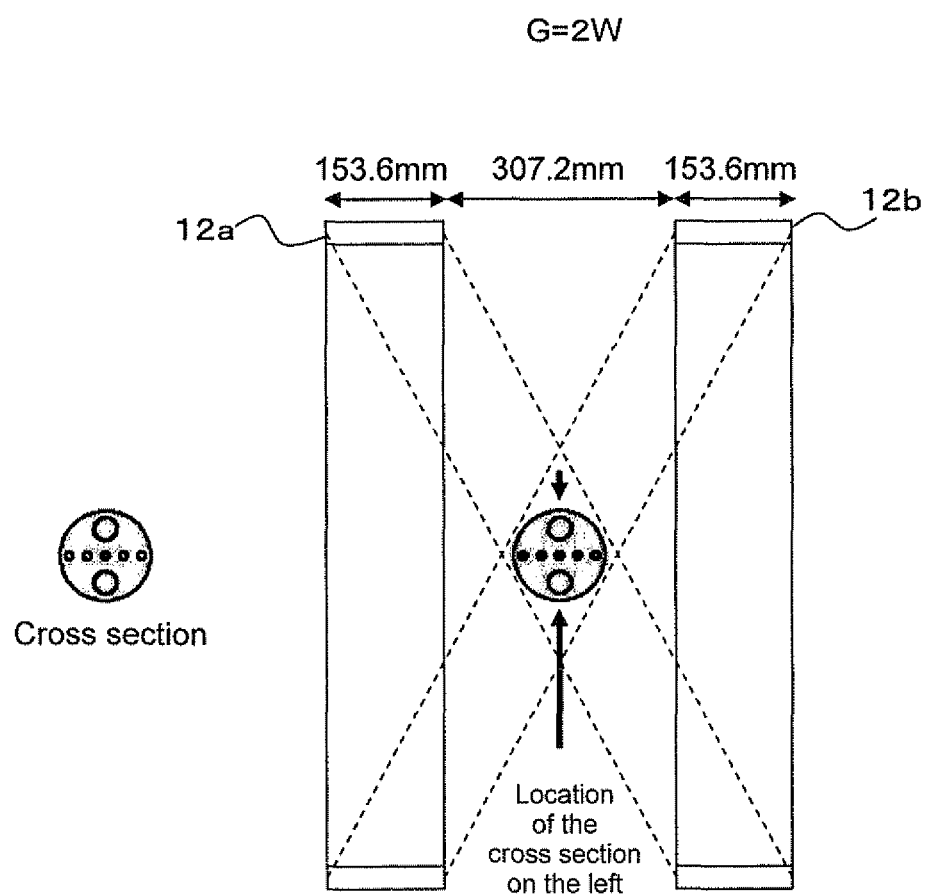
FIG. 11 is a diagram showing the arrangement of the detectors and a cross section of the reconstructed image when measuring the spherical phantom with G=2W.

FIG. 10 shows the result of measurement of the spherical phantom under the condition of G=W. FIG. 11 shows the result of measurement of the spherical phantom under the condition of G=2W. It can be seen that the object, i.e., the irradiation field lying within the open field-of-view can be properly imaged irrespective of the size of G.

Figure 12:
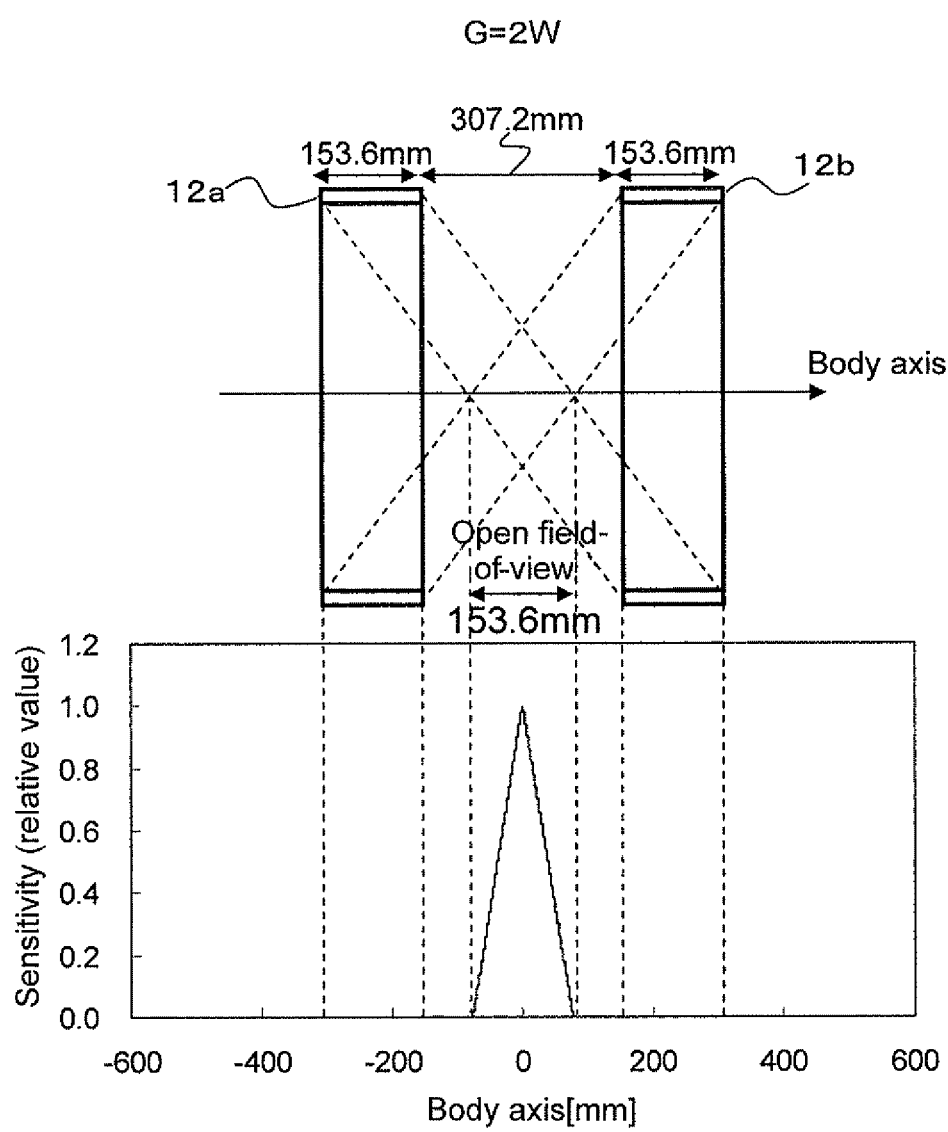
FIG. 12 is a diagram showing the sensitivity distribution with G=2W.

FIG. 12 shows the sensitivity distribution with G=2W. The sensitivity distribution on the body axis is plotted in relative values. The width of the open field-of-view along the body axis is limited to W, or 153.6 mm.

Figure 13:
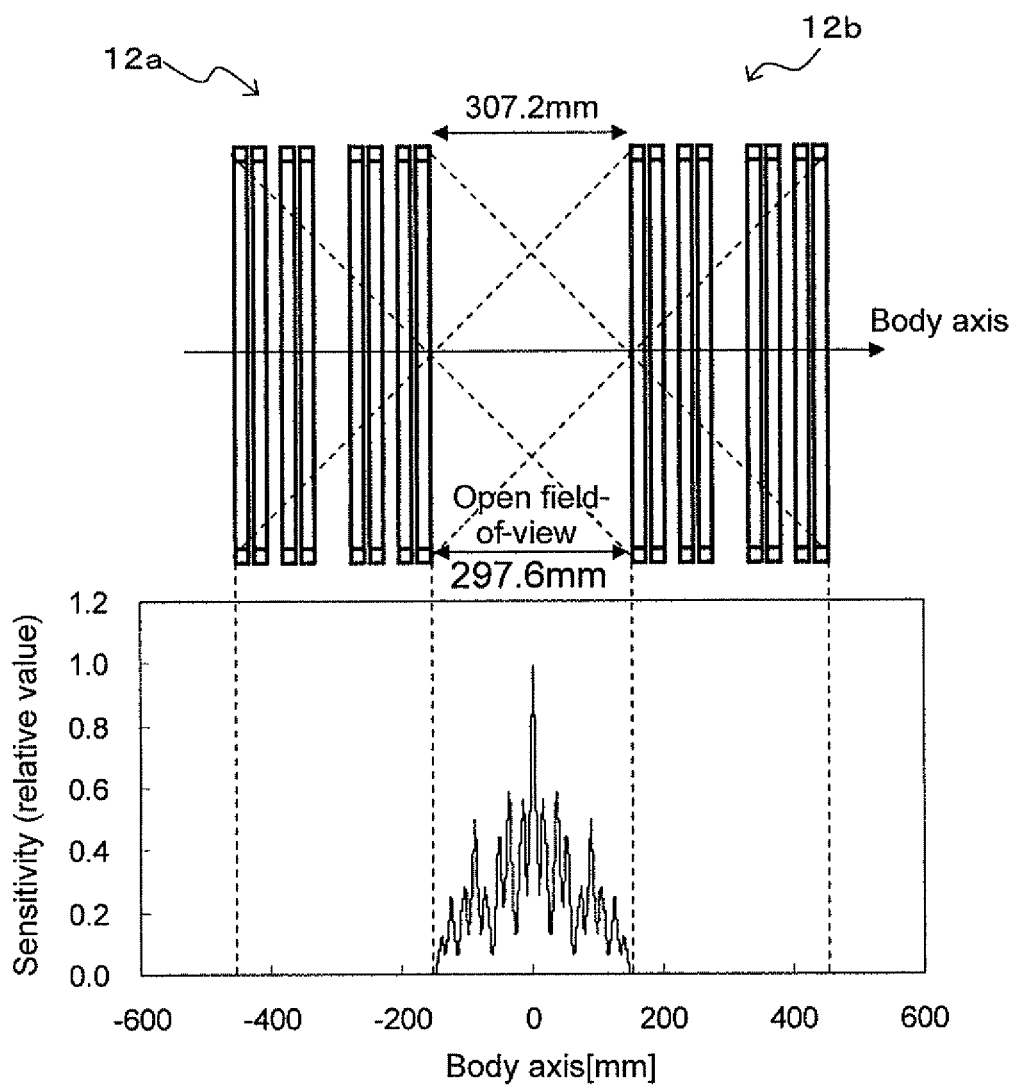
FIG. 13 is a diagram showing a second embodiment of the present invention.

FIG. 13 shows a second embodiment where the detector rings are divided into element detector rings. The right and left detector rings in the second embodiment are each formed by arranging detectors under the condition of D=2, α=0.5, and N=3, with four detection element rings as a unit [0] (W=19.2 mm). While the total number of detection element rings used is the same as in FIG. 12, the open field-of-view is expanded up to 297.6 mm, allowing a greater irradiation field.

Figure 14:
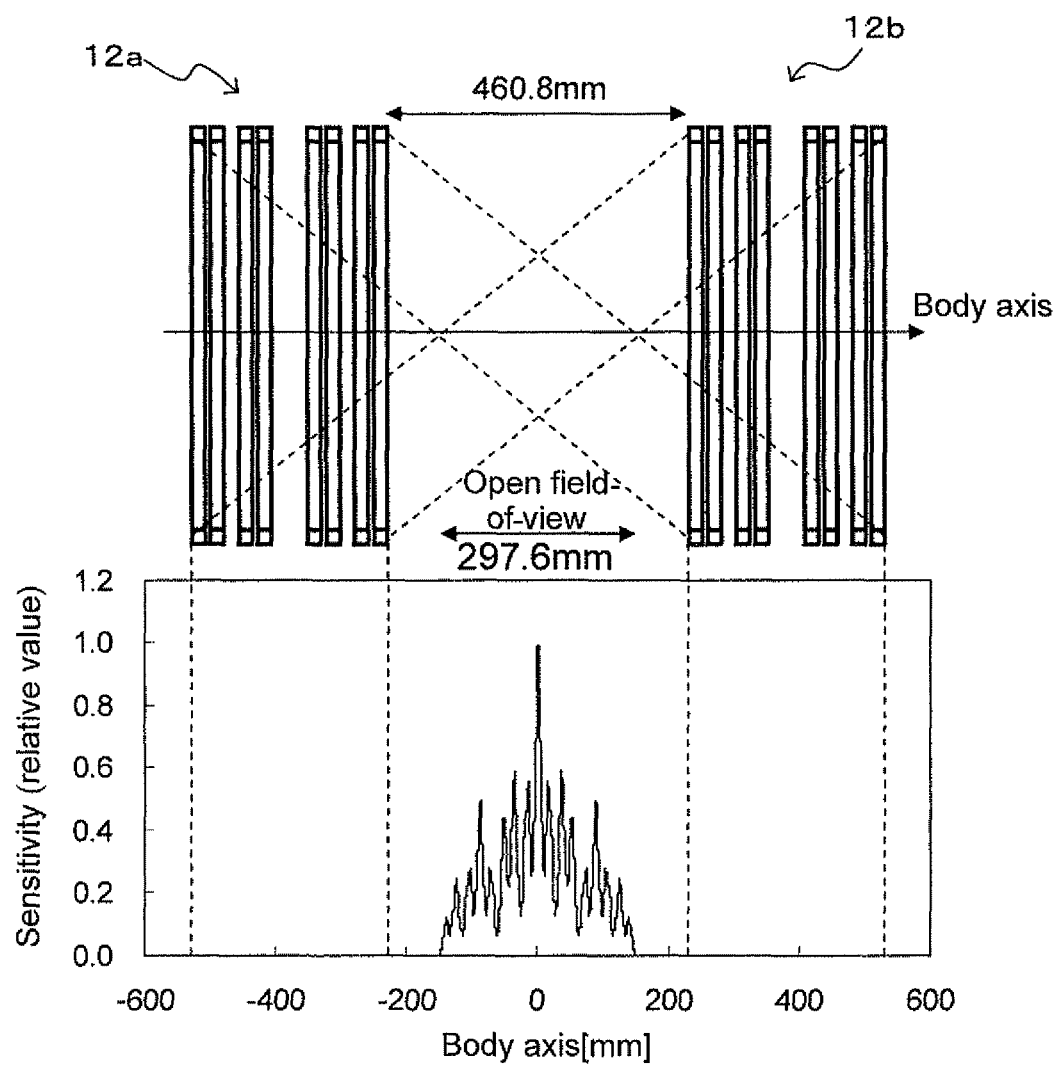
FIG. 14 is a diagram showing a third embodiment of the present invention.

FIG. 14 shows a third embodiment where the detectors are separated farther from the irradiation field in order to avoid a detector effect.

For chest treatment and the like, respiratory and other movements of the affected area need to be taken into account. Specifically, the treatment plan is created so as to administer irradiations in a relatively stable phase of breathing such as the expiratory state in the respiratory cycles. In treatment, respiration monitoring is performed to detect the motion of a marker or the like attached to the chest, and irradiation is administered only when the respiratory phase coincides with that on the treatment plan.

Figure 15:
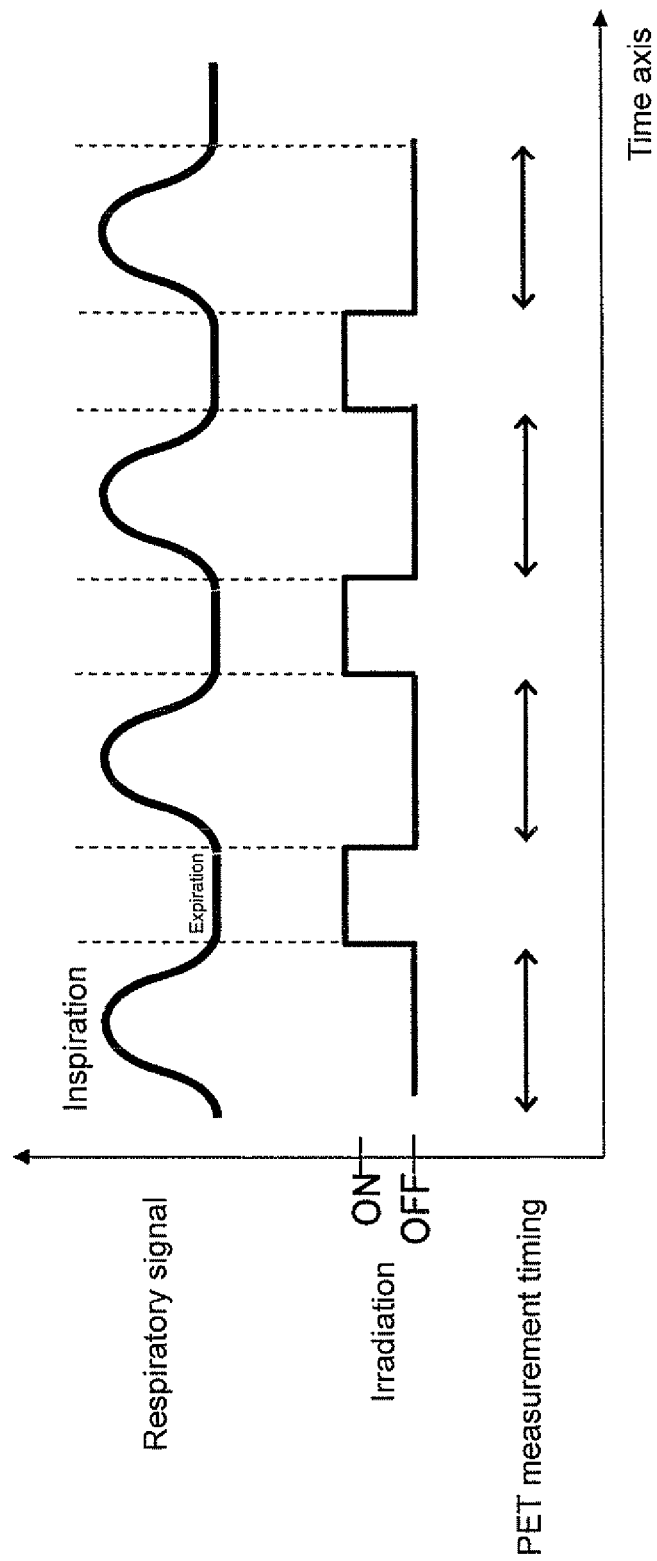
FIG. 15 is a chart showing an example of respiratory-gated control.

FIG. 15 shows the control of turning ON the irradiation depending on the expiratory phase of the respiratory signal. Here, PET measurement can be performed at the timing when the irradiation is OFF (inspiratory phase). This allows efficient PET measurement in the middle of a series of irradiations.

Figure 16:
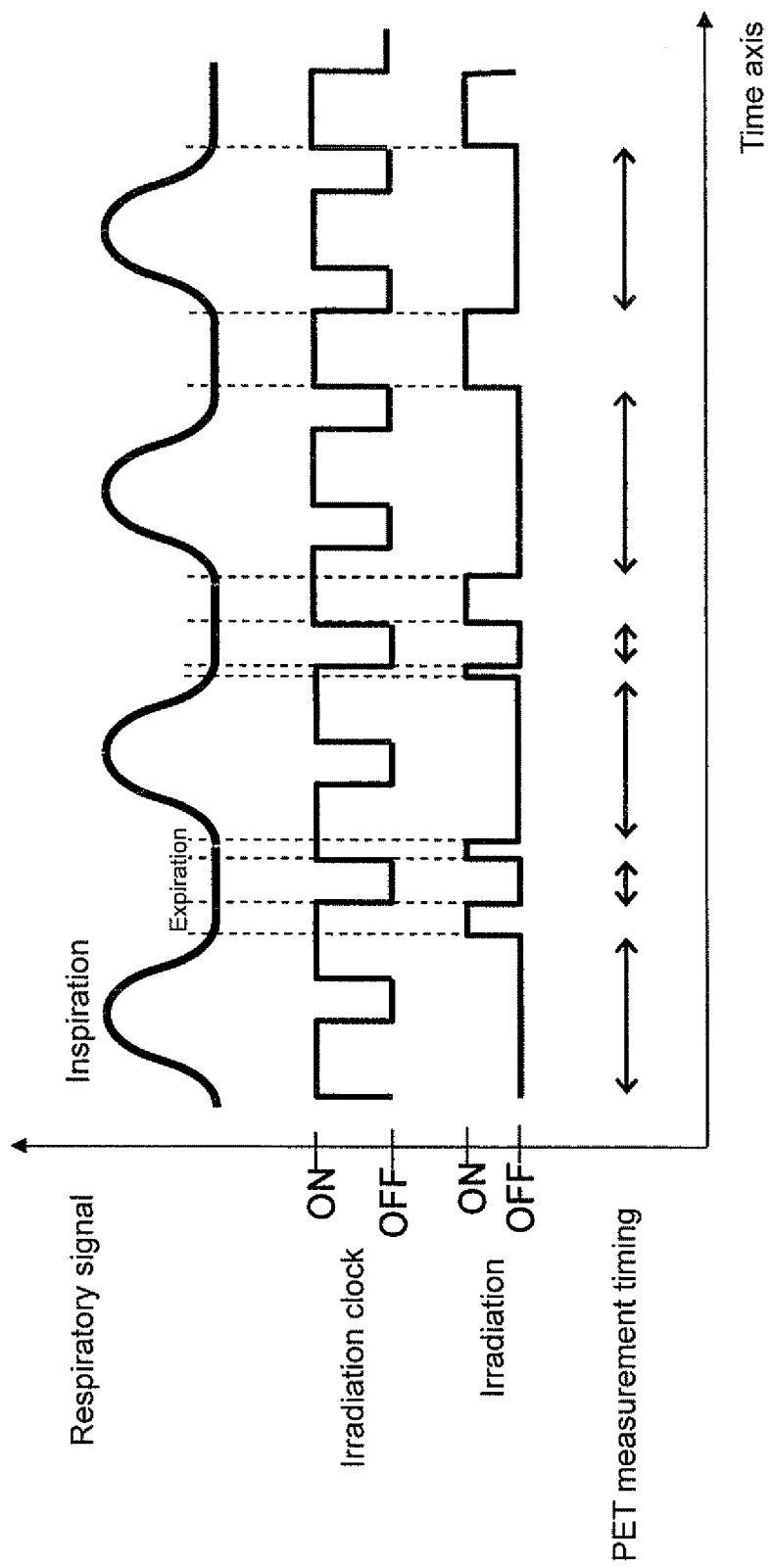
FIG. 16 is a chart showing another example of the respiratory-gated control.

FIG. 15 is predicated on the case that the irradiation beam can be continuously produced from the accelerator. However, the irradiation beam may be produced intermittently in a periodic manner. FIG. 16 shows the latter case where respiratory-gated irradiation is performed. The irradiation can be performed only when the expiratory phase coincides with the irradiation clock. While the timing available for irradiation is limited as compared to the case of FIG. 15, the timing available for PET measurement increases and it is possible to reduce the PET measurement time. It should be appreciated that the body motions to be taken into account for treatment are not limited to respirations but include heartbeats and other motions.

Figure 17:
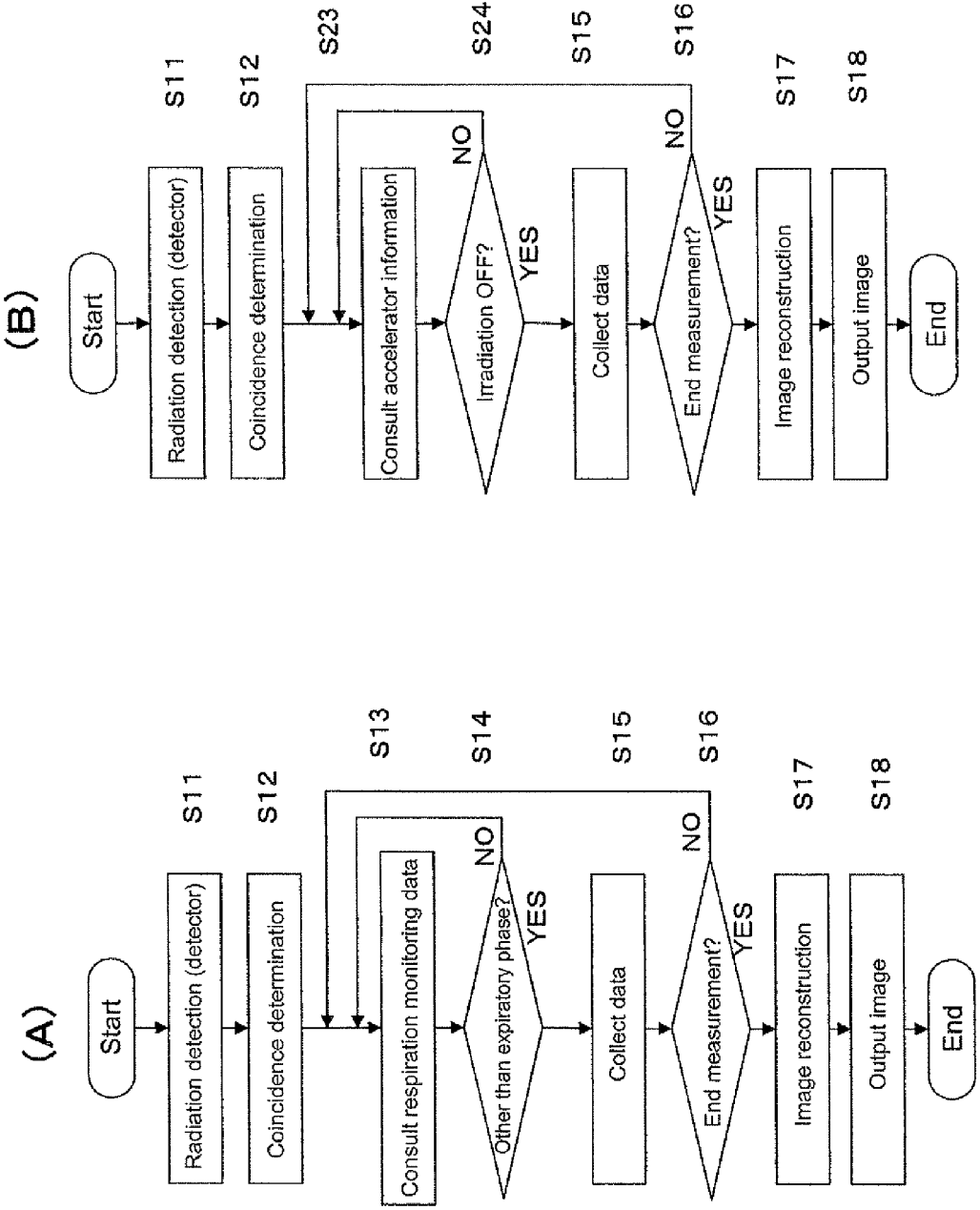
FIG. 17 is a flowchart showing the operation of the respiratory-gated control.

According to a flowchart shown in FIG. 17(A), the detectors initially detect radiations (S11). A coincidence determination is made by known techniques (S12). At the same time, respiration monitoring data which is obtained by detecting and analyzing the motions of the marker arranged in the vicinity of the radiation irradiation area is consulted (S13). A phase other than expiratory phases is selected (S14), and data that is determined to be coincident is collected (S15). When the irradiation is ended and the measurement is ended (S16), image reconstruction is performed based on the collected data (S17) and the image is output (S18).

There has so far been no case where the PET measurement is applied to respiratory-gated irradiation. The flowchart shown in FIG. 17(B) shows a known technology for ordinary non-respiratory-gated irradiation, where accelerator information is consulted at step S13 instead of the respiration monitoring data. According to the present invention, the consultation of the respiration monitoring data makes it possible to acquire synchronous data for PET measurement easily without interfering with the irradiation system. In addition, PET image reconstruction can be performed in each respiratory phase to suppress respiration-based fluctuations of the PET image.

It should be noted that the rings are not limited to the circular shape, but may have an octagonal, hexagonal, or other polygonal shape.

INDUSTRIAL APPLICABILITY

It becomes possible to image the condition of an affected area and a treatment beam for monitoring in radiation therapy of irradiating the affected area with X-rays, gamma rays, or particle beams.

The invention claimed is:

1. A combined radiation therapy/PET apparatus comprising:
an open PET device having multi-ring detector rings that are opposed to each other in a direction of a body axis so as to leave a first gap greater than a width of each detector ring therebetween; and
a radiation therapy device that irradiates an affected area with a radiation beam for radiation therapy through said first gap, wherein
a region of interest within said first gap and lying in an irradiation field of the radiation therapy is covered by a field-of-view of the open PET device, and
in at least one of the detector rings, a predetermined number of element detector units each including a predetermined number of detection element rings are arranged with a second gap therebetween so that said second gap is smaller than or equal to an average width of two element detector units that form said second gap.

2. The combined radiation therapy/PET apparatus according to claim 1, wherein
said second gap of a first ring set in which the gap is smaller than or equal to an average width of two element detector units that form said second gap,
a second ring set that is made to include a predetermined number of element detector units, and
the first ring set and the second ring set are arranged to leave a third gap of equal to or less than an average of the widths of the first ring set and the second ring set.

3. The combined radiation therapy/PET apparatus according to claim 1, wherein said first gap of the open PET device in the direction of the body axis is variable.

4. The combined radiation therapy/PET apparatus according to claim 1, wherein the open PET device is configured such that, if a first detector ring and a second detector ring divided by said first gap that includes the irradiation field have the same size with a diameter D1=D2 and a length W1=W2 and are arranged with said first gap G therebetween, an open field-of-view has a diameter DO and length WO:

$WO = W1$, and $DO = W1 \cdot D1/(G+W1)$.

5. The combined radiation therapy/PET apparatus according to claim 1, wherein the open PET device is configured such that, when a first detector ring and a second detector ring form said first gap that includes the irradiation field, coincidence measurement is performed only between the first detector ring and the second detector ring, not within the first detector ring or within the second detector ring.

6. The combined radiation therapy/PET apparatus according to claim 1, wherein in respiratory-gated irradiation where irradiation is performed with the radiation beam in synchronization with a respiratory phase, the open PET device is configured such that, a PET measurement is performed in time with intervals between beam irradiations.

7. The combined radiation therapy/PET apparatus according to claim 1, wherein a configuration of the detector rings is different from one detector ring to another.

* * * * *